(12) United States Patent
Letlow

(10) Patent No.: US 6,315,422 B1
(45) Date of Patent: Nov. 13, 2001

(54) REAR AND SIDE VIEW MIRROR DEVICE

(76) Inventor: Justin S. Letlow, 1496 NE. Elgin, Bend, OR (US) 97701

( * ) Notice: Subject to any disclaimer, the term of this patent is extended or adjusted under 35 U.S.C. 154(b) by 0 days.

(21) Appl. No.: 09/697,982

(22) Filed: Oct. 26, 2000

(51) Int. Cl.⁷ .................................................. G02B 7/182
(52) U.S. Cl. ......................... 359/871; 359/872; 359/873; 359/874; 359/875
(58) Field of Search ........................................ 359/871, 872, 359/873, 874, 875, 876; 248/476, 477, 479, 489

(56) References Cited

U.S. PATENT DOCUMENTS

| | | |
|---|---|---|
| D. 401,019 | 11/1998 | Felicetta . |
| 1,324,133 | 12/1919 | Roy . |
| 1,748,034 | 2/1930 | Blackman . |
| 1,817,401 | 8/1931 | Ward . |
| 1,989,437 | 1/1935 | Weisz . |
| 2,119,208 | 5/1938 | Goldsmith . |
| 5,946,150 * | 8/1999 | Liao ...................................... 359/871 |
| 6,027,219 * | 2/2000 | Arambulo ............................. 359/872 |

* cited by examiner

*Primary Examiner*—Mohammad Sikder

(57) ABSTRACT

A rear and side view mirror device for allowing one to inspect one's ear for certain buildup of wax and dirt. The rear and side view mirror device includes an elongate support assembly including an elongate support member having ends; and also includes connectors being pivotally attached to the elongate support assembly; and further includes mirror members being pivotally attached to the connectors.

10 Claims, 2 Drawing Sheets

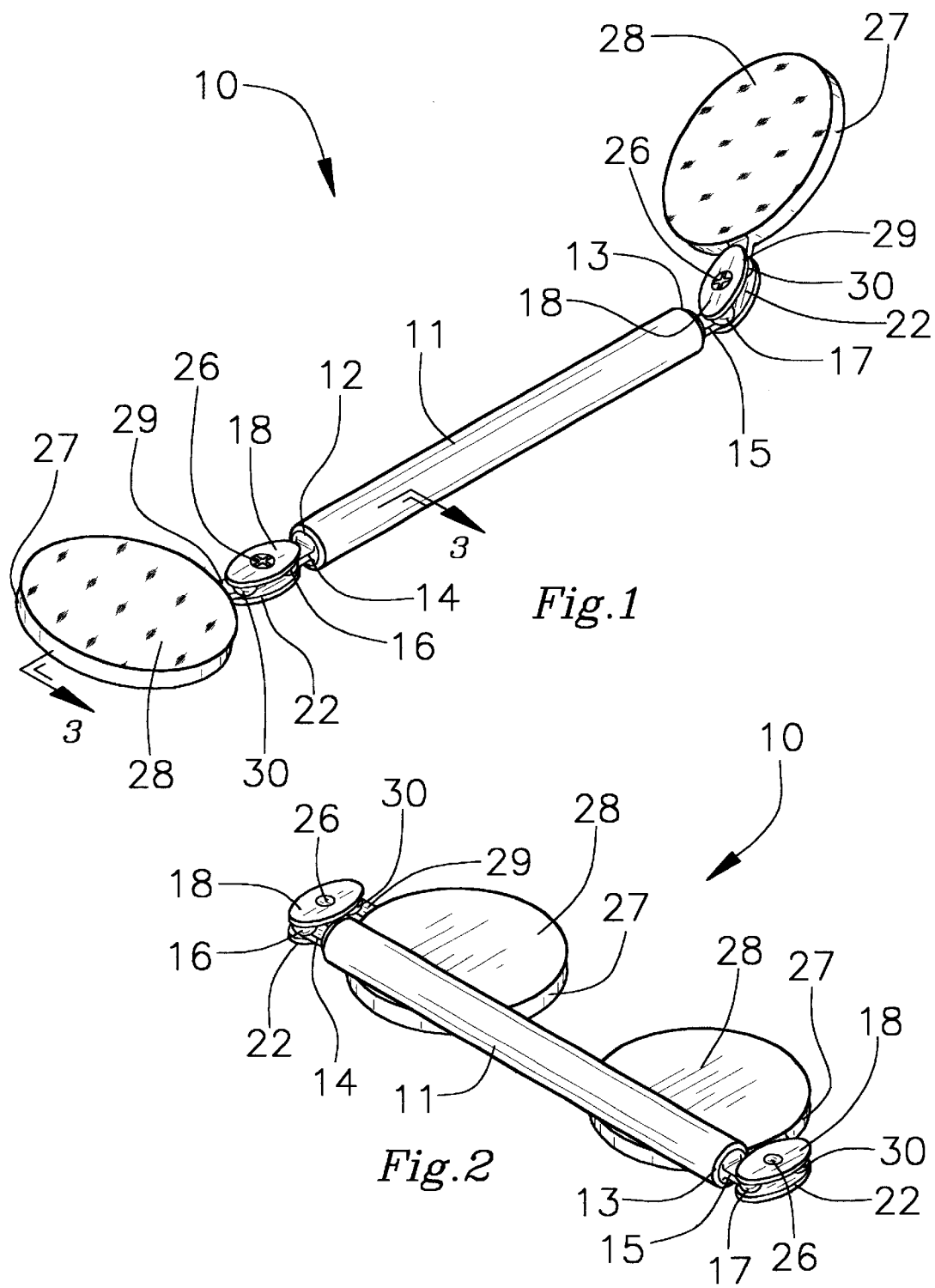

REAR AND SIDE VIEW MIRROR DEVICE

BACKGROUND OF THE INVENTION

1. Field of the Invention

The present invention relates to a rear and side viewing mirror and more particularly pertains to a new rear and side view mirror device for allowing one to inspect one's ear for certain buildup of wax and dirt.

2. Description of the Prior Art

The use of a rear and side viewing mirror is known in the prior art. More specifically, a rear and side viewing mirror heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 2,119,208; 1,817,401; 1,748,034; 1,324,133; 1,989,437; and U.S. Pat. No. Des. 401,019.

While these devices fulfill their respective, particular objectives and requirements, the aforementioned patents do not disclose a new rear and side view mirror device. The inventive device includes an elongate support assembly including an elongate support member having ends; and also includes connectors being pivotally attached to the elongate support assembly; and further includes mirror members being pivotally attached to the connectors.

In these respects, the rear and side view mirror device according to the present invention substantially departs from the conventional concepts and designs of the prior art, and in so doing provides an apparatus primarily developed for the purpose of allowing one to inspect one's ear for certain buildup of wax and dirt.

SUMMARY OF THE INVENTION

In view of the foregoing disadvantages inherent in the known types of rear and side viewing mirror now present in the prior art, the present invention provides a new rear and side view mirror device construction wherein the same can be utilized for allowing one to inspect one's ear for certain buildup of wax and dirt.

The general purpose of the present invention, which will be described subsequently in greater detail, is to provide a new rear and side view mirror device which has many of the advantages of the rear and side viewing mirror mentioned heretofore and many novel features that result in a new rear and side view mirror device which is not anticipated, rendered obvious, suggested, or even implied by any of the prior art rear and side viewing mirror, either alone or in any combination thereof.

To attain this, the present invention generally comprises an elongate support assembly including an elongate support member having ends; and also includes connectors being pivotally attached to the elongate support assembly; and further includes mirror members being pivotally attached to the connectors.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new rear and side view mirror device which has many of the advantages of the rear and side viewing mirror mentioned heretofore and many novel features that result in a new rear and side view mirror device which is not anticipated, rendered obvious, suggested, or even implied by any of the prior art rear and side viewing mirror, either alone or in any combination thereof.

It is another object of the present invention to provide a new rear and side view mirror device which may be easily and efficiently manufactured and marketed.

It is a further object of the present invention to provide a new rear and side view mirror device which is of a durable and reliable construction.

An even further object of the present invention is to provide a new rear and side view mirror device which is susceptible of a low cost of manufacture with regard to both materials and labor, and which accordingly is then susceptible of low prices of sale to the consuming public, thereby making such rear and side view mirror device economically available to the buying public.

Still yet another object of the present invention is to provide a new rear and side view mirror device which provides in the apparatuses and methods of the prior art some of the advantages thereof, while simultaneously overcoming some of the disadvantages normally associated therewith.

Still another object of the present invention is to provide a new rear and side view mirror device for allowing one to inspect one's ear for certain buildup of wax and dirt.

Yet another object of the present invention is to provide a new rear and side view mirror device which includes an elongate support assembly including an elongate support member having ends; and also includes connectors being pivotally attached to the elongate support assembly; and further includes mirror members being pivotally attached to the connectors.

Still yet another object of the present invention is to provide a new rear and side view mirror device that is easily and conveniently adjustable and contortable to fit one's need.

Even still another object of the present invention is to provide a new rear and side view mirror device that allows the user to easily examine areas of one's own body.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a new rear and side view mirror device according to the present invention.

FIG. 2 is another perspective view of the present invention.

DESCRIPTION OF THE PREFERRED EMBODIMENT

Figure 3:
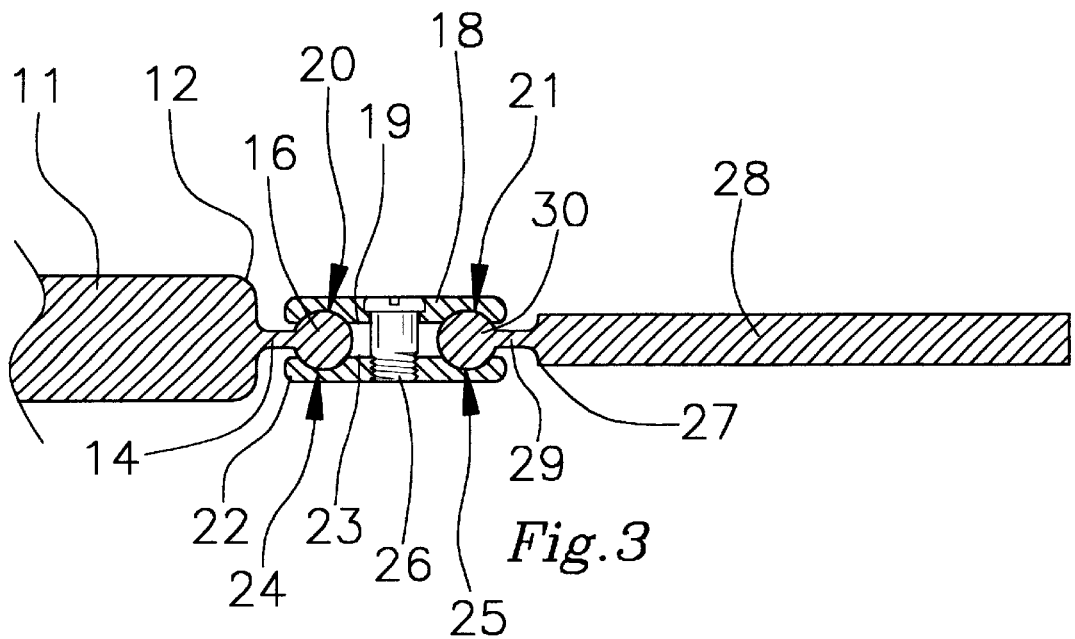
FIG. 3 is a cross-sectional view of the present invention.
Figure 4:
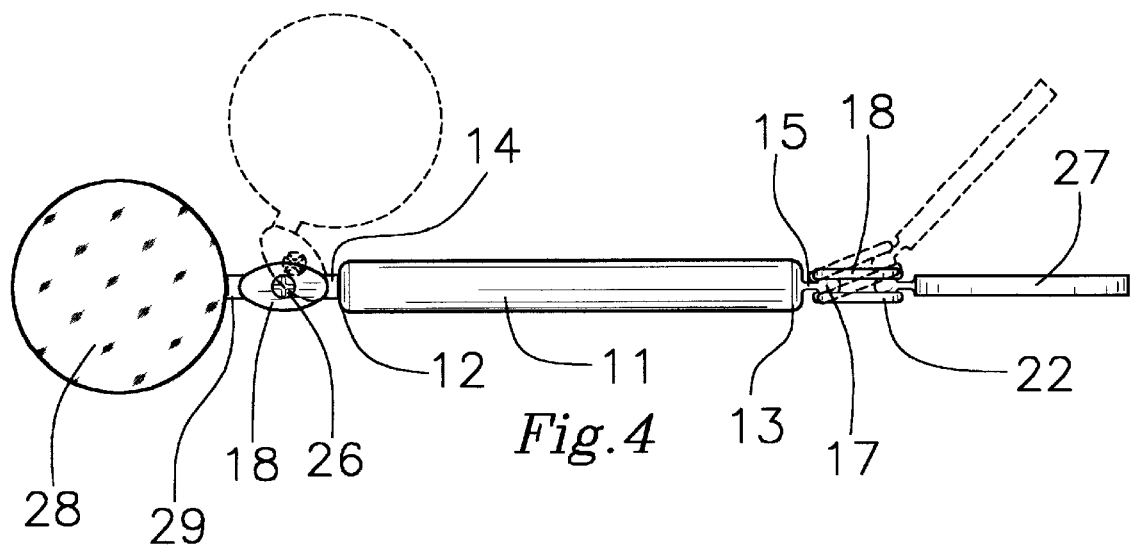
FIG. 4 is a side elevational view of the present invention.

With reference now to the drawings, and in particular to FIGS. 1 through 4 thereof, a new rear and side view mirror device embodying the principles and concepts of the present invention and generally designated by the reference numeral 10 will be described.

As best illustrated in FIGS. 1 through 4, the rear and side view mirror device 10 generally comprises an elongate support assembly including an elongate support member 11 having ends 12,13. The elongate support assembly further includes shaft members 14,15 integrally extending outwardly and co-axially from the ends 12,13 of the elongate support member 11, and also includes ball members 16,17 being securely and integrally attached to outer ends of the shaft members 14,15.

Connectors are pivotally attached to the elongate support assembly. Each of the connectors includes a first plate member 18 and a second plate member 22 being spaced apart and being fastened together with a fastening member 26. Each of the plate members 18,22 has a pair of recessed portions 20,21,24,25 being spaced apart and being disposed in a side 19,23 thereof. Each of the recessed portions 20,21 of the first plate member faces and is aligned to a respective recessed portion 24,25 of the second plate member 22 thus forming a socket therebetween. Each of the connectors includes a pair of sockets.

Mirror members are pivotally attached to the connectors. Each of the mirror members includes a frame 27, an image-reflective member 28 conventionally mounted to the frame 27, a shaft 29 being securely and conventionally attached to and extending outwardly from the frame 27, and a ball 30 being securely and integrally attached to an outer end of the shaft 29. Each of the ball members 16,17 is movably received in one of the sockets of a respective connector, and each of the balls 30 is movably received in the other of the sockets of a respective connector. The mirror members are adjustable toward and away from the elongate support member 11 and are rotatable relative to the elongate support member 11.

In use, the user can easy adjust and position the mirror members according to one's need by moving and pivoting the mirror members relative to the connectors and to the elongate support member 11 so that the user can look into one of the mirror members and also see into the other mirror member to view one's side or rear.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A rear and side view mirror device comprising:
an elongate support assembly including an elongate support member having ends;
connectors being pivotally attached to said elongate support assembly; and
mirror members being pivotally attached to said connectors;
wherein each of said connectors defines a pair of joints for maximizing freedom of movement of said mirror members with respect to said elongate support assembly, a first one of each said pair of joints being connected to said elongate support member and a second one of said pair of joints being connected to one of said mirror members.

2. A rear and side view mirror device as described in claim 1, wherein said elongate support member further includes shaft members extending outwardly and co-axially from said ends of said elongate support member, and also includes ball members being securely attached to outer ends of said shaft members.

3. A rear and side view mirror device as described in claim 1, wherein each of said connectors includes a first plate member and a second plate member being spaced apart and fastened together with a fastening member, each of said plate members has a pair of recessed portions disposed in a side thereof.

4. A rear and side view mirror device as described in claim 3, wherein each of said recessed portions of said first plate member faces and is aligned to a respective said recessed portion of said second plate member thus forming a socket of one of said joints therebetween.

5. A rear and side view mirror device as described in claim 4, wherein each of said connectors includes a pair of said sockets forming said pair of joints.

6. A rear and side view mirror device as described in claim 4, wherein each of said mirror members include a frame, an image-reflective member mounted to said frame, a shaft being securely attached to and extending outwardly from said frame, and a ball being securely attached to an outer end of said shaft.

7. A rear and side view mirror device as described in claim 6, wherein each of said ball members is movably received in one of said sockets of a respective said connector, and each of said balls is movably received in the other of said sockets of a respective said connector, said mirror members being adjustable toward and away from said elongate support member and being rotatable relative to said elongate support member into a position wherein said elongate support member overlaps both of said mirror members in a compact arrangement.

8. A rear and side view mirror device as described in claim 1, wherein each of said connectors permits a range of motion of said elongate support assembly with respect to said connector of approximately 180 degrees and each of said connectors permits a range of motion of a connected one of said mirror members with respect to said connector of approximately 180 degrees.

9. A rear and side view mirror device as described in claim 8, wherein each of said mirror members has a shaft, and wherein the shaft of each of said mirror members is positionable substantially parallel and adjacent to a longitudinal axis of said elongate support assembly to define a collapsed position of said mirror members.

10. A rear and side view mirror device as described in claim 9, wherein each of the shafts of said mirror members is positionable in substantially parallel to and collinear with said elongate support member to define an extended position of said mirror members.

\* \* \* \* \*